United States Patent

Jacquet et al.

[11] 4,107,290
[45] Aug. 15, 1978

[54] ANTI-SOLAR POLYMERS, METHOD OF MAKING THE SAME AND COSMETIC COMPOSITIONS CONTAINING THE SAME

[75] Inventors: Bernard Jacquet, Antony; Christos Papantoniou, Epinay-sur-Seine; Pierre Dufaure; Claude Mahieu, both of Paris, all of France

[73] Assignee: L'Oreal, Paris, France

[21] Appl. No.: 715,566

[22] Filed: Aug. 18, 1976

Related U.S. Application Data

[63] Continuation-in-part of Ser. No. 374,059, Jun. 27, 1973, Pat. No. 3,992,356.

[30] Foreign Application Priority Data
Jul. 29, 1976 [FR] France .................. 76 23175
Jun. 29, 1972 [LU] Luxembourg ............ 65622

[51] Int. Cl.² .......................... A61K 7/42; A61K 7/44
[52] U.S. Cl. .......................... 424/47; 424/59; 424/60; 424/78; 526/265; 526/259; 526/329; 526/328; 526/304; 526/312; 526/270; 526/266; 526/280; 526/298; 526/326; 526/330; 526/327; 526/248; 526/313; 526/268; 526/320; 526/264; 526/40; 526/46; 526/245; 526/322; 526/292; 526/56; 260/875
[58] Field of Search ................ 424/59, 60, 47; 526/258, 259, 304, 310, 322

[56] References Cited

U.S. PATENT DOCUMENTS

| | | | |
|---|---|---|---|
| 2,853,423 | 9/1958 | La Via | 424/47 |
| 3,946,035 | 3/1976 | Jacquet et al. | 526/259 |
| 4,004,074 | 1/1977 | Gerecht et al. | 424/59 |

Primary Examiner—Joseph L. Schofer
Assistant Examiner—Peter F. Kulkosky
Attorney, Agent, or Firm—Cushman, Darby & Cushman

[57] ABSTRACT

An anti-solar polymer has in the macromolecular chain thereof at least one unit of the formula

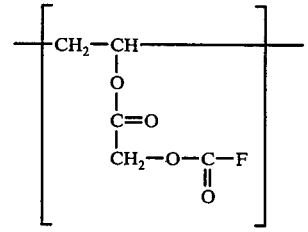

wherein F is a residue derived from an aromatic compound.

The anti-solar polymer can also be one having in the macromolecular chain thereof at least one unit of the formula

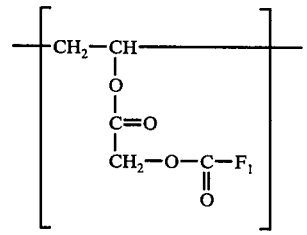

wherein $F_1$ is

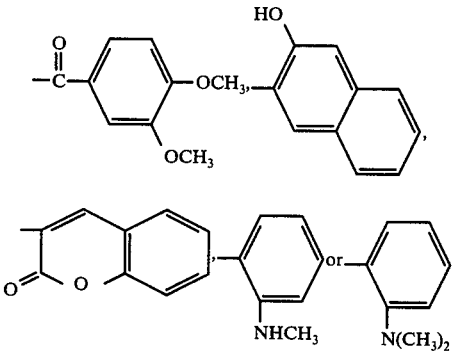

These polymers have the ability to absorb wave lengths in the range of about 280–315 millimicrons. The polymers are employed in a cosmetic composition.

11 Claims, No Drawings

ANTI-SOLAR POLYMERS, METHOD OF MAKING THE SAME AND COSMETIC COMPOSITIONS CONTAINING THE SAME

This application is a continuation-in-part of our application Ser. No. 374,059, filed June 27, 1973, now U.S. Pat. No. 3,992,356.

The present invention relates to novel "anti-solar" polymers which are particularly useful in cosmetic preparations, to the process for preparing these new polymers and to cosmetic compositions containing the same.

Sunburn, or erythema, results from the excessive exposure of human skin to the rays of the sun and the wave lengths of light in the range of 280 to 315 millimicrons, often called the "erythematous zone" are those which produce such sunburn.

Below this wave length range the sun rays do not present any particular danger, for they are filtered by the ozone in the atmosphere.

However, the UV rays which are responsible for or which produce a desirable suntan are those in the zone ranging from 315 to 400 millimicrons.

Consequently, if one desires to be exposed to solar radiation, it is important that the skin be protected with the aid of a composition containing a substance which absorbs the UV rays in the erythematous zone, thereby avoiding an undesirable sunburn, which composition however also transmits those wave lengths in the range of 315 to 400 millimicrons so as to obtain a desirable suntan.

Heretofore a number of formulations have been proposed for this purpose. For the most part, they are based on aromatic compounds exhibiting an absorption in the UV in the zone between 280 and 315 millimicrons and, more particularly, between 295 and 305 millimicrons.

In addition to this absorbing power, such compounds must have other properties and in particular they must not absorb the wave lengths of light in the zone ranging from 315 to 400 millimicrons, they should be non-volatile and they should also be resistant to both fresh and salt water and to perspiration. Additionally they should exhibit cosmetic compatibility with other components which may be present in suntan formulations and they should be non-odorous, non-toxic and non-irritating, i.e. entirely harmless to the user.

Among these characteristics, non-toxicity and dermotological compatibility are of great importance.

Representative aromatic compounds which have heretofore been employed in suntan preparations include derivatives of para-aminobenzoic acid, derivatives of anthranilic acid, derivatives of cinnamic acid and dihydroxy and trihydroxy cinnamic acid, derivatives of coumarin and the like.

The rather current widespread use of such compounds as an "anti-solar filter", is not without certain disadvantages. Certain of these substances do not exhibit sufficient efficiency in their ability to absorb the wave lengths of light in the erythematous zone. Moreover many do not possess the requisite solubility characteristics necessary so as to be utilized in many different types of formulation, and finally, because of their low molecular weight, many are able to penetrate through the epidermis of the skin into the human body which, in certain cases, can cause unfavorable side effects.

In an effort to remedy the inconveniences of these compounds, it has also been proposed to fix on macromolecular chains of certain copolymers, filters absorbing in UV in the erythematous region.

Among the polymers of this type described in the literature, one can in particular cite those resulting from the polymerization of 2-hydroxy (3-acryloxy or methacryloxy-2-hydroxy-4-propoxy) benzophenone with a comonomer of the methyl methacrylate type or of an unsaturated carboxylic acid such as acrylic, methacrylic, itaconic or crotonic acid, or the like.

However, these copolymers have not been found to be fully effective in cosmetic compositions because often they are quite difficult to formulate with other components generally found in a wide variety of anti-solar compositions and often they absorb only a portion of the undesirable wave lengths in the erythematous zone.

In effect, the nature of the function which permits the linking of the filter moiety to the polymeric chain of these known materials seriously limits the number of aromatic residues which impart the filtering or absorbing characteristics to the polymer and thus it has been found that there is often not a sufficient amount of such aromatic residues to provide the degree of efficacy desired or required.

To overcome these disadvantages, the applicants have now provided anti-solar ploymers wherein the residue which imparts to the polymer the ability to absorb wave lengths in the erythematous zone is linked to the polymeric chain by an intermediate chemical function of a particular type.

Thus, in a first embodiment, the present invention relates to an anti-solar polymer which contains in the macromolecular chain thereof at least one unit having the formula

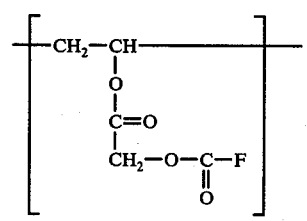

I wherein F is a residue derived from an aromatic compound imparting to the polymer the ability to absorb those wave lengths of light in the range of about 280 and 315 millimicrons.

In a second embodiment of the present invention, the anti-solar polymer contains in the macromolecular chains thereof at least one unit having the formula:

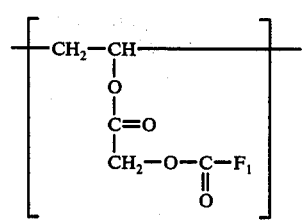

II wherein $F_1$ represents a member selected from the group consisting of

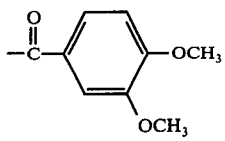  (1)

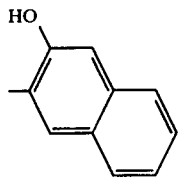  (2)

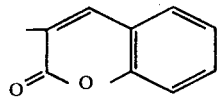  (3)

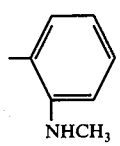  (4)

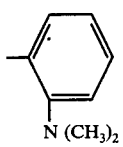  (5)

Representative anti-solar polymers of the first embodiment include:
N-vinylpyrrolidone/vinyloxycarbonylmethyl 2-cyano-3,3-diphenyl acrylate; and
vinyl stearate/vinyloxycarbonylmethyl 2-cyano-3,3-diphenyl acrylate.

These two particular copolymers are obtained by using, as the aromatic ultra-violet absorbing compound, 2-cyano-3,3-diphenyl acrylic acid.

The new polymers according to this embodiment of the invention are preferably copolymers (bipolymer, terpolymers, etc.), that is they carry both the units of formula II and one or several other units derived from ethylenically unsaturated monomers.

It has been observed that the use of the anti-solar polymers of the present invention in cosmetic compositions is highly advantageous since the linking of the F or $F_1$ residue to the macromolecular chain avoids or at least significantly retards the migration of an otherwise non-linked absorbent moiety through the skin into the human body thereby avoiding any undesirable side effects which have been experienced in the use of heretofore known anti-solar filters.

The importance of this feature can be easily appreciated especially since repeated applications of the anti-solar compositions of this invention are generally not necessary to achieve the desired results which thereby avoids any substantial risk of a massive absorption of the filter compounds into the body.

The anti-solar polymers of this invention generally have an average molecular weight generally between 2000 and 1,000,000. The radical in formula I above, represented by F, can be derived from a variety of aromatic compounds. Representative radicals include aryl, alkyl aryl, alkenylaryl, each of which can optionally be substituted, as well as aromatic heterocylic radicals, also optionally substituted.

In particular the radical F can be selected from the group consisting of:

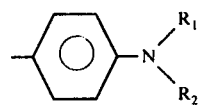  (1)

wherein $R_1$ and $R_2$ represent alkyl having 1-4 carbon atoms;

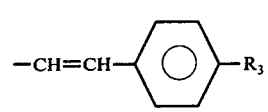  (2)

wherein $R_3$ represents hydrogen or methoxy;

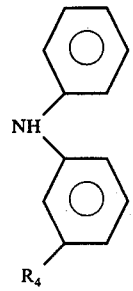  (3)

wherein $R_4$ represents — S — $CF_3$ or — $CF_3$;

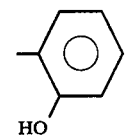  (4)

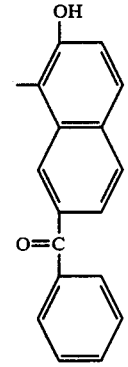  (5)

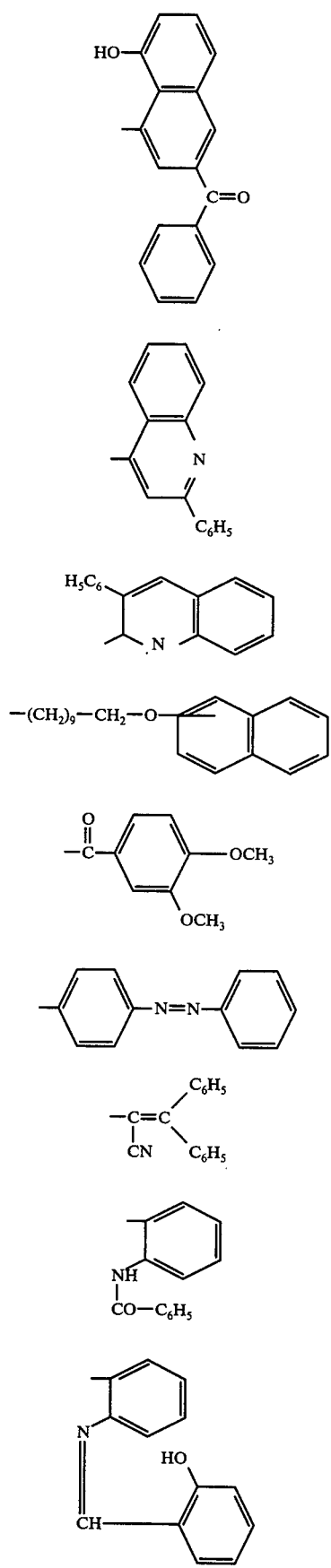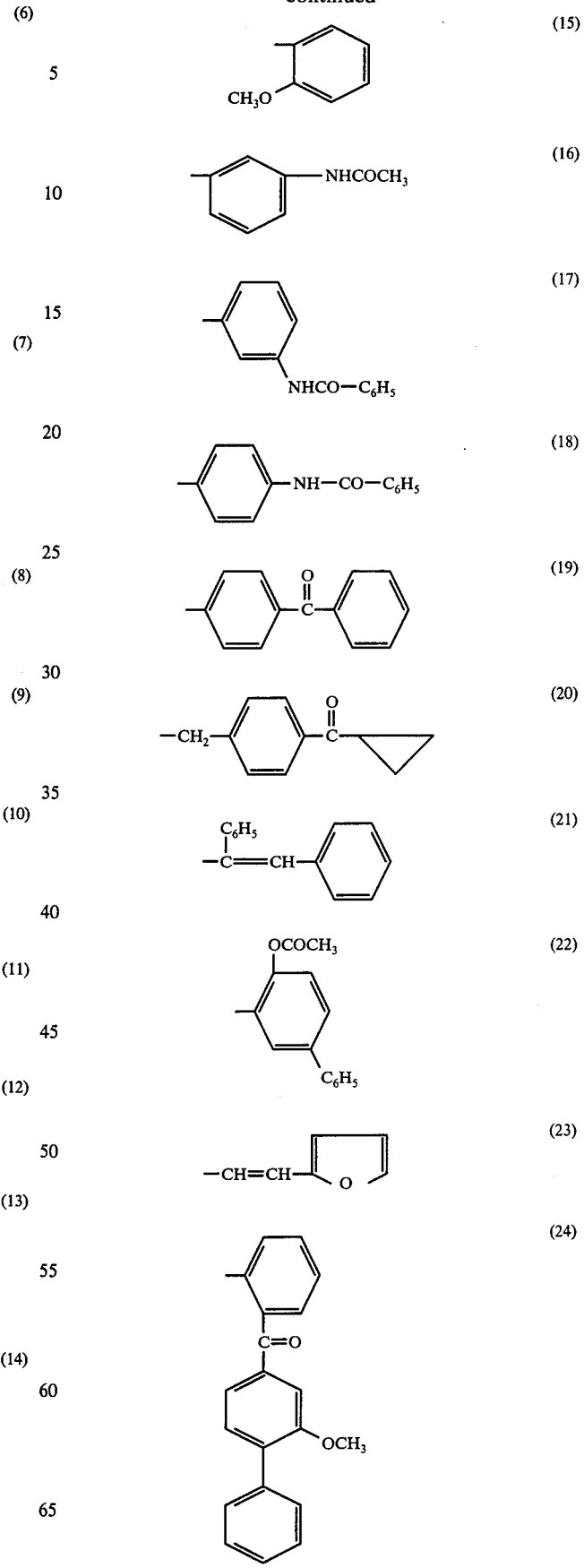

-continued

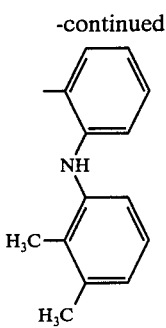
(25)

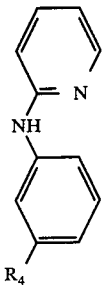
(26)

wherein R₄ has the meaning given above,

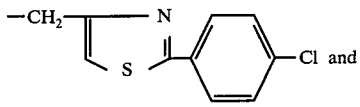
(27)

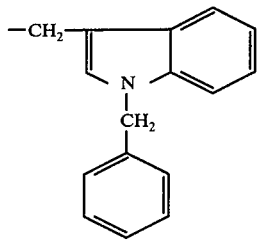
(28)

Because of the variety of the nature of the radicals F and $F_1$ that can be linked to the polymer chain, it is possible to fully cover the erythematous zone simply by a judicious selection of the appropriate compounds to be linked to said polymer chain.

The anti-solar polymers of the present invention can be either homopolymers, copolymers, terpolymers and the like.

Thus, in the homopolymers of this invention, in the repeating unit defined by formulas I and II the values of F and $F_1$ are the same whereas in a group of copolymers of this invention, in the said repeating unit, the values of F and/or $F_1$ can be different.

The ability to obtain copolymers having fixed on their macromolecular chains F and/or $F_1$ radicals or differing structures is a highly desirable feature since by choosing the appropriate compounds, it is thus possible to provide a single copolymer which can cover the entire erythematous zone, thereby producing an anti-solar filter of great efficacy.

The polymers of the invention can also be bipolymers, terpolymers or the like, and they can include, at the same time, (1) units of formula I or II wherein F or $F_1$ is the same, and one or more other units can be derived from ethylenically unsaturated monomers, or (2) units of formula I or II wherein the F and/or $F_1$ radicals are different, and one or more other units can be derived from ethylenically unsaturated monomers.

The selection of the ethylenically unsaturated monomers or comonomers for use in the production of the polymers of the present invention is generally dependent on the function of the desired use of the resulting composition or, more exactly, on the type of formulation that is desired. The amount of ethylenically unsaturated monomer in the copolymer is about 20–90 percent of the total wegiht of the copolymer.

Thus it is possible to impart to the anti-solar polymers of this invention different characteristics by varying the nature of the comonomer used.

Representative comonomers include:
 (a) N-vinylpyrrolidone,
 (b) N-methacryloyl D-glucosamine,
 (c) dimethylaminoethyl methacrylate
 (d) stearyl methacrylate
 (e) stearyl acrylate and
 (f) vinyl stearate The first three of these comonomers generally increase the solubility of the resulting polymer in aqueous solutions while the last three ordinarily increase the solubility of the polymer in oil.

In another embodiment of the present invention the copolymers can have the formula

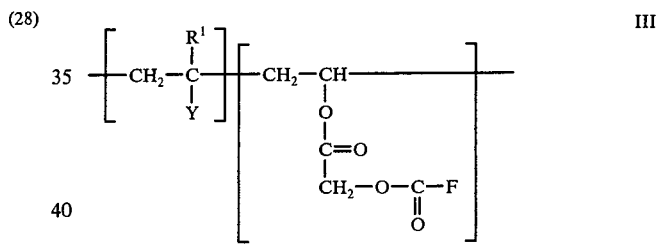
III wherein
F has the meaning given above,
$R^1$ represents hydrogen or methyl and
Y represents a radical selected from the group consisting of

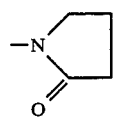
(i)

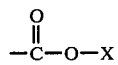
(ii)

wherein X represents D-glucosamine, dimethylamino ethyl optionally quaternized and $C_{18}H_{37}$, and

(iii)

In yet another embodiment of the present invention, the copolymers can have the formula:

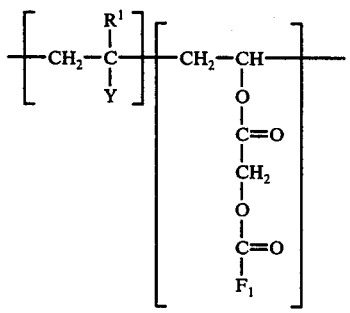

wherein

F₁ has the meaning given above,
R¹ represents hydrogen or methyl and
Y represents a member selected from the group consisting of

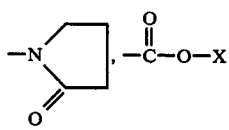

wherein X represents dimethylamino ethyl optionally quaternized and $C_{18}H_{37}$,

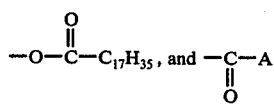

wherein A is D-glucosamine radical.

According to this embodiment, the anti-solar polymers have a content of units of formula II generally between 15 and 100%, and preferably between 20 and 80% by weight, relative to the total weight of the polymer.

The amount of the comonomer present in the anti-solar polymer of formula III of the present invention is variable but it is generally between about 20 and 90% of the total weight of the polymer, and preferably between 20 and 85%.

This latter content, as can be seen, can vary rather widely and the particular content selected can depend, for instance, on the particular use chosen for the resulting polymer.

Also, the anti-solar polymers of formula II are characterized in that the weight of the repeating unit is between about 10-100%, generally between 15-100% of the total weight of the polymer, and preferably between 20 and 80%.

The present invention also relates to a process for preparing the said anti-solar polymers.

In one embodiment the polymers of formulas I and II can be prepared according to two distinct processes.

(1) The first process comprises homopolymerizing or copolymerizing in a first stage one or more comonomers with a monomer of the formula

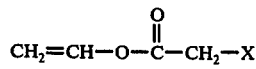

wherein X is a halogen, and in a second stage, reacting the thus formed homopolymer or copolymer with at least one alkaline salt of an aromatic compound of the formula

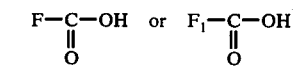

wherein F and F₁ have the same meanings given above, in amounts corresponding to the desired polymer.

(2) The second process comprises preparing in a first stage a monomer, designated a "solar-filter monomer", of the formula

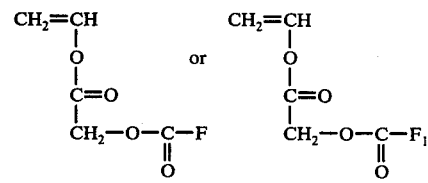

wherein F and F₁ have the same meanings given above, either of these said monomers in a second stage then being homopolymerized or copolymerized with one or more other comonomers.

In these two processes, the polymerization reactions are identical and can be effected according to conventional polymerization reactions, i.e. in mass, in solution, in suspension or in emulsion.

The polymerization initiators utilized are generally conventional free radical polymerization initiators and the choice of any one particular initiator can depend principally on the different monomers used as well as on the nature of reaction medium selected.

Representative usable initiators include the peroxides, such as benzoyl peroxide, lauroyl peroxide, acetyl peroxide, tertiobutyl hydroperoxide or benzoyl hydroperoxide, a catalyst which by decompositon liberates an inert gas, such as azobisisobutyonitrile, an oxidation-reduction catalyst such as sodium persulfate, sodium sulfite and $H_2O_2$. The concentration of the initiator is generally between about 0.2–35 weight percent, preferably between 0.5–20 weight percent, of the total weight of the monomer content.

The molecular weight of the anti-solar polymers of the present invention can be regulated by introducing, during the course of polymerization reaction, small amounts, i.e. about 0.05–0.15 weight percent of a chain regulating agent such as an aldehyde, for instance, butyraldehyde or a halogenated substance such as chloroform, bromoform, carbon tetrachloride, and the like.

At the end of the polymerization reaction, the polymer obtained can, if desired, be purified by, for example, treating it with an ion exchange resin.

The present invention also relates to an anti-solar cosmetic composition containing as the active component for absorbing wave length of light in the range of 280 to 315 millimicrons at least one anti-solar polymer as described above.

These cosmetic compositions can be present in diverse forms, the choice of any particular form being dependent upon the desired use of the composition. Preferably, these compositions are present in the form of an aqueous emulsion, lotion, cream, milk, gel or in the form of an aerosol. These compositions can also be present in the form of an aqueous or hydroalcoholic (ethanol or isopropanol) solution or even in the form of an oily solution.

When the compositions of the present invention are present in the form of an aerosol, they are packaged under pressure in a conventional aerosol bomb or container in the presence of a propellant gas which is preferably a

EXAMPLE 4

Preparation of a copolymer of vinyloxycarbonylmethyl cinnamate/dimethylaminoethyl methacrylate (Process 2)

2 g of vinyloxycarbonyl methyl cinnamate, prepared in accordance with Example 1, are copolymerized with 1 g of dimethylaminoethyl methacrylate in solution in 6 g of dioxane, in the presence of 0.3 g of azobis-isobutyronitrile.

The resulting solution is agitated for 24 hours at 80° C. There is then introduced 1 g of dimethyl sulfate in solution in 48 g of methanol.

The temperature is maintained for 4 hours at 80° C, and the polymer is then precipitated in ethyl acetate, yielding 1.3 g of pure polymer.

$\lambda_{max}^{EtOH-H_2O} = 276$ millimicrons
$K_{sp} = 9,000$

EXAMPLE 5

Preparation of a copolymer of vinyloxycarbonylmethyl 4-methoxy cinnamate/vinyl stearate (Process 1)

Into a 500 ml flask provided with a condenser, a nitrogen lead in tube and an agitator, and containing 88 g of sodium hydride in a 50% suspension in oil and 100 g of dimethylformamide, there are slowly introduced 18 g of 4-methoxy cinnamic acid in solution in 70 ml of dimethylformamide.

The resulting mixture is agitated initially for 24 hours at ambient temperature and then at 140° C for 8 hours. There are then introduced 40 g of a copolymer composed of 30% vinyl chloroacetate and 70% vinyl stearate (MW = 40,000) in solution in 100 ml of dimethylformamide. The mixture is agitated at 140° C for 15 hours after which the polymer is precipitated in 2 liters of water, taken up in hot benzene, filtered and precipitated in methanol, yielding 40 g of pure polymer.

$\lambda_{max\ 1}^{Hexane} = 298$ millimicrons
$K_{sp} = 37,000$
$\lambda_{max\ 2}^{Hexane} = 306$ millimicrons
$K_{sp} = 37,000$

EXAMPLE 6

Preparation of a copolymer of vinyloxycarbonylmethyl 4-methoxy cinnamate/dimethylaminoethyl methacrylate quaternized with dimethyl sulfate (Process 1)

The same quantity of solution of sodium 4-methoxy cinnamate, prepared in Example 5, is poured into a flask containing 40 g of a copolymer composed of 30% vinyl chloroacetate and 70% dimethylaminoethyl methacrylate quaternized with dimethyl sulfate (MW = 50,000) in solution in 100 ml of dimethylformamide.

The resulting mixture is agitated at 140° C for 15 hours, after which the polymer is precipitated in petroleum ether, yielding 25 g of pure polymer.

$\lambda_{max\ 1}^{EtOH-H_2O} = 298$ millicron
$K_{sp} = 32,000$
$\lambda_{max\ 2}^{EtOH-H_2O} = 306$ millimicrons
$K_{sp} = 32,000$

EXAMPLE 7

Preparation of vinyloxycarbonylmethyl-4-N,N-dimethylamino benzoate of the formula

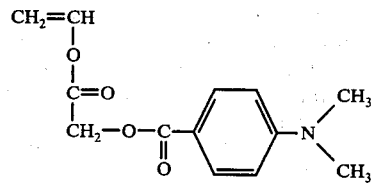

Into a 125 ml reactor provided with a condenser, a nitrogen lead in tube and an agitator and containing 1.66 g of sodium hydride (50% suspension in oil) and 20 g of dimethylformamide, there is introduced, little by little, a solution of 6.6 g of 4-N,N-dimethylamino benzoic acid in solution in 30 g of dimethylformamide while maintaining the temperature at 30° C by cooling the same.

The solution is left to stand with stirring for 12 hours. Then there are introduced 4.8 g of vinyl chloroacetate and the mixture is left to stand for 12 hours at ambient temperature.

The solution is poured into water and the resulting precipitate is filtered and dried under reduced pressure. After recrystallization in methanol, 4.8 g of pure product are obtained.

Melting point = 80° C
$\lambda_{max}^{EtOH} = 313$ millimicrons

EXAMPLE 8

Preparation of a copolymer of vinyloxy carbonylmethyl-4-N,N-dimethylamino benzoate, 2.5 g of stearyl methacrylate, 0.25 g of azobis-isobutyronitrile and 12 ml of benzene The solution is heated for 16 hours at 80° C, then poured into 800 ml of a 50:50 mixture of ethanol and methanol, yielding 2 g of pure product.

$\lambda_{max}^{CHCl_3} = 311$ millimicrons
$K_{sp} = 20,400$

EXAMPLE 9

Preparation of a copolymer of vinyloxycarbonylmethyl-4-N,N-dimethylamino benzoate/N-vinylpyrrolidone (Process 1)

Into a 100 ml flask provided with a condenser, a nitrogen lead in tube and an agitator and containing 1.66 g of sodium hydride (50% suspension in oil) and 20 g of dimethylformamide, there is introduced, little by little, a solution of 6.6 g of 4-N,N-dimethylamino benzoic acid in solution in 30 ml of dimethylformamide while maintaining the temperature at 30° C, by cooling.

The solution is left to stand at rest for 12 hours. There are then introduced 10 g of a copolymer composed of 35% vinyl chloroacetate and 65% N-vinylpyrrolidone (MW = 40,000) in 50 ml of dimethylformamide.

The resulting solution is left to stand for 24 hours at 50° C after which it is poured into 2 liters of sulfuric ether. The resulting precipitate is filtered and then dried under reduced pressure, yielding 8 g of pure product. MW = 30,000.

$\lambda_{max}^{EtOH} = 312$ mm
$K_{sp} = 41,000$

EXAMPLE 10

Preparation of a copolymer of vinyloxycarbonylmethyl-4-N,N-dimethylamino benzoate/vinyl stearate (Process 1)

Into a 100 ml flask provided with a condenser a nitrogen lead in tube and an agitator and containing 0.48 g of sodium hydride (50% suspension in oil) and 20 ml of dimethylformamide, there are introduced 1.65 g of 4-N,N-dimethylamino benzoic acid in solution in 20 ml of dimethylformamide.

The reaction is exothermic and the temperature is maintained at 40° C by cooling.

The resulting solution is agitated for 24 hours at ambient temperature after which there are introduced 4 g of a copolymer composed of 30% vinyl chloroacetate and 70% of vinyl stearate (MW - 40,000) in solution in 20 ml of dimethylformamide. The temperature is held at 100° C for 24 hours and then the solution is poured into methanol.

The resulting precipitate, after filtration, is dried under reduced pressure, yielding 1.5 g of pure polymer.

$\lambda_{max}^{Hexane} = 303$ millimicrons
$K_{sp} = 37,000$

EXAMPLE 11

Preparation of a copolymer of vinyloxycarbonylmethyl 4-N,N-dimethylamino benzoate/dimethylaminoethyl methacrylate quaternized with dimethyl sulfate (Process 2)

2 g of vinyloxycarbonylmethyl 4-N,N-dimethyl benzoate, prepared according to Example 7, are copolymerized with 1 g of dimethylaminoethyl methacrylate in solution in 6 g of dioxane in the presence of 0.3 g of azobis-isobutyronitrile.

The resulting solution is agitated for 24 hours at 80° C. There is then introduced 1 g of dimethyl sulfate in solution in 4 g of methanol. The temperature is held at 80° C for 4 hours after which the polymer is precipitated in ethyl acetate, yielding 1.1 g of pure polymer.

$\lambda_{max}^{EtOH-H_2O} = 313$ millimicrons
$K_{sp} = 30,000$

EXAMPLE 12

Preparation of vinyloxycarbonyl methyl salicylate of the formula

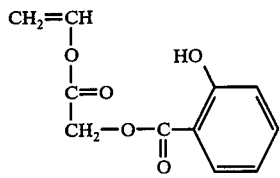

Into a 250 ml flask provided with a condenser, a nitrogen lead in tube and an agitator, there are introduced 16 g of sodium salicylate, 12 g of vinyl chloroacetate and 30 g of dimethylformamide.

The resulting solution is left to stand with agitation for 3 days at ambient temperature after which it is poured into chloroform.

After the addition of sulfuric ether thereto and after decanting the same, the etherified layers are separated and washed with water.

The ether is then distilled off to provide an oil which is purified by distillation (12 g).

Boiling point = 120°–124° C under 0.05 mm Hg
$\lambda_{max}^{MeOH} = 305$ millimicrons

EXAMPLE 13

Preparation of a copolymer of vinyloxycarbonylmethyl salicylate/vinyl stearate (Process 2)

Into a 25 ml flask provided with a condenser, a nitrogen lead in tube and an agitator, there are introduced 2 g of vinyloxycarbonylmethyl salicylate, 1 g of vinyl stearate and 0.3 g of azobis-isobutyronitrile and 6 ml of acetone.

The mixture is heated to reflux for 24 hours, after which it is poured into methanol. The resulting precipitate is then filtered and dried, yielding 1.2 g of pure polymer.

$\lambda_{max}^{CHCl_3} = 309$ millimicrons
$K_{sp} = 11,300$

EXAMPLE 14

Preparation of copolymer of vinyloxycarbonylmethyl salicylate/vinyl stearate (Process 1)

Into a 50 ml flask provided with a condenser, a nitrogen lead in tube and an agitator, there are introduced 1.6 g of sodium salicylate, 4 g of a copolymer composed of 30% vinylchloroacetate and 70% of vinyl stearate (MW = 40,000) and 20 g of dimethylformamide.

The temperature is held at 140° C for 15 hours, at which time a portion of the dimethylformamide is distilled off and the remaining solution is poured into lukewarm napthonol.

3.6 g of pure polymer are obtained.

$\lambda_{max}^{Hexane} = 309$ millimicrons
$K_{sp} = 7,300$

EXAMPLE 15

Preparation of a copolymer of vinyloxycarbonylmethyl salicylate/stearyl methacrylate (Process 2)

Into a 25 ml flask provided with a condenser, a nitrogen lead in tube and an agitator, there are introduced 2 g of vinyloxycarbonylmethyl salicylate, 1 g of stearyl methacrylate, 0.3 g of azobis-isobutyronitrile and 3 ml of acetone.

The resulting mixture is heated at reflux for 24 hours after which it is poured into methanol. The resulting precipitate is filtered and then dissolved in chloroform and reprecipitated in methanol, yielding 1.5 g of pure polymer.

$\lambda_{max}^{CHCl_3} = 309$ millimicrons
$K_{sp} = 11,000$

EXAMPLE 16

Preparation of a copolymer of vinyloxycarbonylmethyl salicylate/dimethylaminoethyl methacrylate quaternized with dimethyl sulfate (Process 1)

2 g of vinyloxycarbonylmethyl salicylate prepared in accordance with Example 12, are copolymerized with 1 g of dimethylaminoethyl methacrylate in solution in 6 g of dioxane in the presence of 0.3 g of azobis-isobutyronitrile.

The solution is agitated for 24 hours at 80° C after which there is introduced 1 g of dimethyl sulfate in solution in 4 g of methanol. The temperature is held for 4 hours at 80° C. The polymer is then precipitated with ethyl acetate, yielding 1 g of pure polymer.

$\lambda_{max}^{EtOH-H_2O} = 304$ millimicrons
$K_{sp} = 11,000$

EXAMPLE 17

Preparation of a copolymer of vinyloxycarbonylmethyl flufenate/N-vinylpyrrolidone (Process 1)

(a) Preparation of copolymer of N-vinylpyrrolidonevinyl chloroacetate

Into a 1 liter flask, provided with a condenser filled with solid carbon dioxide, a nitrogen inlet, a dropping funnel and a mechanical agitator, there are introduced 1 g of azobis-isobutyronitrile in solution in 100 g of absolute ethanol, 63.2 g of N-vinylpyrrolidone and 36.8 g of vinyl chloroacetate.

The resulting solution is heated at 80° C for 9 hours with agitation. After 1 hour of the polymerization reaction, the reaction mixture thickens. There are then introduced through the dropping funnel 200 ml of absolute ethanol over a one hour period.

The polymer is obtained under the form of a powder by pouring the ethanolic solution into sulfuric ether. Then the resulting polymer is redissolved in ethanol and reprecipitated in sulfuric ether, filtered and dried at 40° C under reduced pressure.

Yield = 75%; MW = 40,000 by osmometry in solution in dioxane.

Elementary analysis shows that the copolymer contains 34% vinylchloroacetate and 66% N-vinylpyrrolidone.

(b) Preparation of the sodium salt of flufenamic acid

Into a 1 liter flask provided with a condenser, a dropping funnel and a nitrogen inlet, there are introduced 10.4 g of sodium hydride (58% suspension in oil) and 200 ml of anhydrous dimethylformamide. Then there is slowly introduced, with agitation, a solution of 70.4 g of 3'-trifluoromethyl-2-carboxylic acid diphenylamine (flufenamic acid) in solution in 300 ml of dimethylformamide. At the end of the addition, the temperature is held at 50° C for 1 hour by means of an oil bath. The mixture is then left to cool with the solution being left to stand at rest overnight.

(c) Reaction of the sodium salt of flufenamic acid with the copolymer of N-vinylpyrrolidone-vinyl chloroacetate 110 g of the copolymer, prepared in accordance with paragraph (a) above, are put into solution in 400 g of dimethylformamide. This solution is introduced into the flask containing the solution of the sodium salt of flufenamic acid. The resulting mixture is then heated by an oil bath at 50° C for 24 hours. The reaction product is then poured, little by little, into 5 liters of water. The resulting white precipitate is filtered, dissolved in acetone and precipitated in sulfuric ether. The polymer thus obtained is dried at 40° C under reduced pressure.

Yield: 80%
Viscosity: 2.34 cps
$\lambda_{max}^{EtOH}$ = 288 millimicrons
$K_{sp}$ = 20,500

Spectrographic content of the polymer in flufenamic acid = 37%.

This polymer can be purified by treating it with an ion exchange resin.

EXAMPLE 18

Preparation of vinyloxycarbonyl-methyl flufenate of the formula:

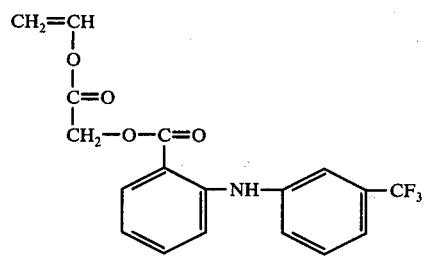

Into a solution of the sodium salt of flufenamic acid, identical to that described in Example 17, paragraph (b), there are slowly introduced 30 g of vinyl chloroacetate diluted with 100 ml of dimethylformamide. The resulting solution is left to stand for 24 hours at ambient temperature with agitation. The mixture is then poured, little by little, into 2 liters of water.

The monomer is isolated under the form of a light yellow powder which is recovered and put into solution in sulfuric ether. The solution is initially washed with N/10 NaOH and then with water until the wash water is neutral. After drying the ether extract on sodium sulfate, the ether is evaporated under reduced pressure, this yielding 60 g of crystalline product which is recrystallized in heptane.

Yield: 66%
Melting point: 61° C
$\lambda_{max\,1}^{Hexane}$ = 221 millimicrons
$\lambda_{max\,2}^{Hexane}$ = 285 millimicrons
$\lambda_{max\,3}^{Hexane}$ = 350 millimicrons

EXAMPLE 19

Preparation of a copolymer of vinyloxycarbonylmethyl flufenate/vinyl stearate (Process 2)

1 g of vinyloxycarbonyl-methyl flufenate, obtained in accordance with Example 18, 1 g of vinyl stearate and 0.2 g of azobis-isobutyronitrile are dissolved in 2 g of acetone. The resulting solution is heated for 24 hours at 80° C, left to cool, and then diluted with 4 g of hexane. The solution obtained is then poured, little by little, into 1 liter of absolute ethanol. The resulting polymer precipitates in the form of a powder and is isolated in a conventional manner. There are thus obtained 1.5 g of pure polymer after drying at 40° C uncer reduced pressure.

$\lambda_{max}^{EtOH}$ = 288 millimicrons
$K_{sp}$ = 20,000

EXAMPLE 20

Preparation of a homopolymer of vinyloxycarbonylmethyl flufenate 70 g of vinyloxycarbonyl-methyl flufenate, obtained in accordance with the process of Example 18, and 3.5 g of azobis-isobutyronitrile are dissolved in 70 g of acetone. The resulting solution is heated at 80° C for 18 hours after which there are introduced 3.5 g of additional azobis-isobutyronitrile. The resulting solution is heated for another 24 hours at the same temperature. The solution thus obtained is diluted with 140 ml of acetone, filtered and poured into 2 liters of absolute ethanol. The resulting polymer is recovered in the form of a white powder which is dissolved in 250 ml of dioxane. On its addition to 2 liters of absolute ethanol, previously maintained at 50° C, the polymer precipitates on cooling.

The precipitated polymer is filtered, and then dried under reduced pressure, yielding 58 g of pure polymer.
Molecular weight = 18,500 (by osometry in solution in toluene).
$\lambda_{max}^{CHCl_3}$ = 288 millimicrons
$K_{sp}$ = 35,000

EXAMPLE 21

Preparation of a copolymer of vinyl stearate/vinyloxycarbonyl-methyl 4-methoxy cinnamate/vinyloxycarbonylmethyl-4-N,N-dimethylamino benzoate/vinyloxycarbonyl-methyl flufenate (Process 1)

Into a 500 ml flask provided with a condenser, a nitrogen lead in tube and an agitator and containing 4.8 g of sodium hydride (50% suspension in oil) and 50 g of dimethylformamide, there are introduced, little by little, 6.8 g of 4-methoxy cinnamic acid, 5 g of 4-N,N-dimethylamino benzoic acid, and 8.4 g of flufenamic acid in solution in 50 g of dimethylformamide. The temperature is maintained at 30° C by cooling.

The mixture is stirred overnight at 50° C, after which there are then introduced 40 g of a polymer composed of 70% vinyl stearate and 30% vinylchloroacetate (MW = 40,000) in solution in 100 g of dimethylformamide.

The resulting solution is agitated for 10 hours at 100° C and the polymer is then precipitated in lukewarm water. After filtering, the polymer is dissolved in benzene and precipitated in methanol. The polymer thus obtained is dried under reduced pressure at 40° C.
$\lambda_{max\ 1}^{CHCl_3}$ = 311 millimicrons
$K_{sp}$ = 28,400
$\lambda_{max\ 2}^{CHCl_3}$ = 300 millimicrons
$K_{sp}$ = 26,200

EXAMPLE 22

Preparation of a copolymer of vinyl stearate/vinyloxycarbonyl-methyl 4-methoxy cinnamate/vinyloxycarbonylmethyl cinnamate/vinyloxycarbonyl-methyl 4-N,N-dimethylamino benzoate (Process 1)

Into a 500 ml flask provided with a condenser, a nitrogen lead in tube and an agitator, and containing 4.8 g of sodium hydride (50% suspension in oil) and 50 g of dimethylformamide, there is introduced, little by solution of 6.8 g of 4-methoxy cinnamic acid, 5 g of 4-N,N-dimethylamino benzoic acid and 4.4 g of cinnamic acid in solution in 50 g of dimethylformamide.

The temperature is maintained at 30° C by cooling. The mixture is then agitated overnight at 50° C, after which there are introduced 40 g of a copolymer composed of 70% vinyl stearate and 30% vinylchloroacetate (MW = 40,000) in solution in 100 g of dimethylformamide.

The solution is agitated for 10 hours at 100° C. The polymer is precipitated in lukewarm, filtered and then dissolved in benzene. The polymer is precipitated again in methanol and dried at 40° C under reduced pressure.
$\lambda_{max}^{CHCl_3}$ = 295 millimicrons
$K_{sp}$ = 28,600
$\lambda_{max\ 2}^{CHCl_3}$ = 310 millimicrons
$K_{sp}$ = 28,600

EXAMPLE 23

Preparation of a copolymer of stearyl acrylate/3-(acrylamidomethylbenzylidene) DL camphor/vinyloxycarbonylmethyl-4-N,N-dimethylamino benzoate (Process 1)

(a) Into a 250 ml flask provided with a condenser, a nitrogen lead in tube and an agitator, there are introduced 10 g of vinyl chloroacetate, 20 g of stearyl arcylate, 10 g of 3-(acrylamido methylbenzylidene) DL camphor, 4 g of azobisisobutyronitrile and 80 g of acetone.

The resulting solution is heated with stirring at the reflux of acetone for 24 hours. On cooling, a precipitate is formed which is redissolved by the addition thereto of chloroform. The solution is filtered and precipitated in absolute ethanol, yielding 25 g of pure polymer.
$\lambda_{max}^{CHCl_3}$ = 295 millimicrons
$K_{sp}$ = 15,700

(b) Into a 100 ml flask, there are introduced 0.48 g of sodium hydride (50% suspension in oil) and 10 g of dimethylformamide. There is then introduced, little by little, a solution of 2 g of 4-N,N-dimethylamino benzoic acid in solution in 10 g of dimethylformamide.

The resulting mixture is left to stand for 24 hours at ambient temperature with stirring.

(c) 12 g of the copolymer obtained in accordance with paragraph (a) are dissolved in 36 g of dimethylformamide and the solution is poured into the mixture obtained in accordance with paragraph (b). The resulting reaction mixture is heated for 10 hours at 50° C, after which it is precipitated in water. After filtering, the polymer obtained is dried under reduced pressure.
$\lambda_{max}^{CHCl_3}$ = 299 millimicrons
$K_{sp}$ = 20,000

EXAMPLE 24

Preparation of N-vinylpyrrolidone/vinyloxycarbonylmethyl 2-cyano-3, 3-diphenyl acrylate Into a round bottom flask there are introduced under nitrogen gas 25 g of dimethyl formamide, 0.66 g of sodium hydride (in a 55% suspension in oil) and 4.13 g of 2-cyano-3, 3-diphenyl acrylic acid while maintaining the temperature at 25° C for 2 hours. The resulting reaction mixture is then heated to 50° C and there are introduced therein 10 g of a copolymer composed of 80% N-vinylpyrrolidone and 20% vinyl chloroacetate, in solution in 40 g of DMF dimethylformamide. The reaction mixture is maintained at 50° C for 24 hours at which time it is cooled and thereafter poured slowly into 700 ml of ethylether. The above polymer which precipitates is then filtered and dried under reduced pressure.

11.5 g of the anti-solar polymer which is soluble in water are obtained.
Yield = 78%
$\lambda_{max}^{DMF}$ = 298 millimicrons;
$K_{sp}$ = 8,850

In a similar manner, by replacing 2-cyano-3,3-diphenyl acrylic acid by an equivalent amount of 3,4-dimethoxy phenylglyoxylic acid, 3-hydroxy-2-naphthoic acid, 3-coumarincarboxylic acid, monomethylanthranilic acid or dimethylanthranilic acid, the following corresponding copolymers are obtained:
copolymer of N-vinylpyrrolidone/vinyloxycarbonylmethyl (3, 4-dimethoxy) phenylglyoxylate;

copolymer of N-vinylpyrrolidone/vinyloxycarbonyl-
methyl (3-hydroxy) 2-naphthoate;

copolymer of N-vinylpyrrolidone/vinyloxycarbonyl-
methyl 3-coumarincarboxylate;

copolymer of N-vinylpyrrolidone/vinyloxycarbonyl-
methyl monomethylanthranilate; and copolymer of N-vinylpyrrolidone/vinyloxycarbonyl-
methyl dimethylanthranilate.

EXAMPLE 25

Preparation of vinyl stearate/vinyloxycarbonylmethyl
2-cyano-3,3-diphenyl acrylate Into a round bottom flask there are introduced under nitrogen gas, 20 g of dimethylformamide, 15.9 g of sodium hydride in a 55% suspension in oil and 89.6 g of 2-cyano-3,3-diphenyl acrylic acid. The resulting mixture is maintained at 25° C for 2 hours; then it is heated to 50° C. Thereafter there are introduced 100 g of a copolymer composed of 60% vinyl stearate and 40% vinyl chloroacetate, in solution in 1 liter of dimethyl formamide, while maintaining the temperature at 50° C for 24 hours. After cooling, the mixture is poured slowly into 10 liters of water, then filtered. The recovered polymer is re-dissolved in a mixture composed of 500 ml of ethyl acetate and 500 ml of chloroform then poured into 6 liters of methanol. 160 g of the anti-solar polymer which is soluble in oil are obtained.

Yield: 87%

$\lambda_{max}^{CHCl_3}$ = 309 millimicrons $K_{sp}$ = 23,800

In a similar fashion, by replacing 2-cyano-3,3-diphenyl acrylic acid with an equivalent amount of (3,4-dimethoxy) phenylglyoxylic acid, 3-hydroxy-2-naphthoic acid, 3-coumarin-carboxylic acid, monomethylanthranilic acid or dimethylanthranilic acid, the following corresponding polymers are obtained:

copolymer of vinyl stearate/vinyloxycarbonylmethyl (3,4-dimethoxy) phenylglyoxylate;

copolymer of vinyl stearate/vinyloxycarbonylmethyl (3-hydroxy)-2-naphthoate;

copolymer of vinyl stearate/vinyloxycarbonylmethyl 3-coumarin-carboxylate;

copolymer of vinyl stearate/vinyloxycarbonylmethyl monomethyl-anthranilate; and copolymer of vinyl stearate/vinyloxycarbonylmethyl dimethylanthranilate.

EXAMPLES OF COSMETIC COMPOSITIONS

EXAMPLES 26-30

An anti-solar oil composition in accordance with the present invention is prepared by admixing the following components:

| Polymer of Example 2 | 10g |
|---|---|
| Perfume | 0.5g |
| Butylated hydroxytoluene (antioxidant) | 0.0625g |
| Colza oil, q.s.p. | 100g |

The above formulation is repeated except that the polymer of Example 2 is replaced by the same quantity of the polymer prepared according to each of Examples 3, 8, 14 and 15. A comparatively advantageous anti-solar oil composition results in each instance.

EXAMPLES 31-34

An anti-solar lotion in accordance with the present invention is prepared by admixing the following components:

| Polymer of Example 5 | 5g |
|---|---|
| Lanolin | 2.5g |
| Butylated hydroxyanisole (antioxidant) | 0.0625g |
| Triglycerides of octanoic and decanoic acids | 40g |
| Ethyl alcohol (96%) q.s.p. | 100g |

The above formulation is repeated except that the polymer of Example 5 is replaced by the same quantity of the polymer prepared according to each of Examples 9, 10 and 13. A comparably advantageous anti-solar lotion results in each instance.

EXAMPLES 35-40

An anti-solar aerosol formulation is prepared by admixing the following components and packaging the same in an aerosol container under pressure:

| Polymer of Example 8 | 5g |
|---|---|
| Absolute ethyl alcohol | 30g |
| Isopropyl myristate | 20g |
| Ricin oil | 2g |
| Lanolin | 2g |
| Perfume | 1g |
| Dichlorodifluoromethane | 40g |

The above aerosol formulation is repeated except that the polymer of Example 8 is replaced by the same quantity of the polymer prepared according to each of Examples 5, 10, 21, 22 and 23. A comparably effective anti-solar aerosol composition results in each instance.

EXAMPLES 41-44

An anti-solar aerosol foam composition according to the present invention is prepared by admixing the following components:

| Polymer of Example 13 | 10g |
|---|---|
| Stearic acid | 0.5g |
| Lauric acid | 0.5g |
| Palmitic acid | 2.5g |
| Vaseline oil | 45.7g |
| Ethyl p-hydroxybenzoate | 0.3g |
| Triethanolamine | 1.5g |
| Reticulated polyacrylic acid, known under the trade name CARBOPOL, (0.05% solution in H$_2$O$_2$)-carboxypolymethylene | 38.5g |
| Perfume | 0.5g |

87g of the above composition are packaged under pressure in a conventional aerosol container or bomb together with 13g of dichlorodifluoromethane.

The above aerosol formulation is repeated except that the polymer of Example 13 is replaced by the same quantity of the polymer prepared in accordance with each of Examples 14, 15 and 19. A comparably effective anti-solar aerosol foam results in each instance.

EXAMPLES 45-46

An anti-solar cream is prepared in accordance with the present invention by admixing the following components:

| | |
|---|---|
| Polymer of Example 10 | 10g |
| Triglycerides of octanoic and decanoic acids | 31g |
| Glycerol monostearate | 6g |
| Polyethylene glycol stearate | 2g |
| Stearic acid | 2g |
| Cetyl alcohol | 1.2g |
| Lanolin | 4g |
| Silicone oil | 1g |
| Methyl p-hydroxybenzoate | 0.3g |
| Propylene glycol | 2g |
| Triethanolamine | 0.1g |
| Perfume | 0.5g |
| Water, q.s.p. | 100g |

The above anti-solar cream formulation is repeated except that the polymer of Example 10 is replaced by the same quantity of the polymer prepared in accordance with Example 17. A comparably effective anti-solar cream results.

EXAMPLE 47

An anti-solar milk is prepared in accordance with the present invention by admixing the following components:

| | |
|---|---|
| Polymer of Example 20 | 5g |
| Cetyl-stearyl alcohol | 2g |
| Cetyl alcohol | 2g |
| Vaseline oil | 20g |
| Lanolin | 4g |
| Stearic acid | 0.5g |
| Silicone oil | 0.3g |
| Propyl p-hydroxybenzoate | 0.4g |
| Glycerin | 5g |
| Reticulated polyacrylic acid sold under the trade name CARBOPOL (carboxypolymethylene) | 0.15g |
| Triethanolamine | 0.20g |
| Perfume | 0.3g |
| Water, q.s.p. | 100g |

EXAMPLES 48-49

An anti-solar cream formulation in accordance with the present invention is prepared by admixing the following components:

| | |
|---|---|
| Polymer of Example 4 | 15g |
| Cetyl-stearyl alcohol | 2g |
| Glycerol monostearate | 4g |
| Cetyl alcohol | 4g |
| Vaseline oil | 5g |
| Butyl stearate | 5g |
| Propylene glycol | 7g |
| Silicone oil | 0.125g |
| Non-ionic polymer of high molecular weight sold under the trade name POLYOX (5% solution in $H_2O_2$) | 3.5g |
| Methyl p-hydroxybenzoate | 0.3g |
| Perfume | 0.4g |
| Water, q.s.p. | 100g |

The above anti-solar cream formulation is repeated except that the polymer of Example 4 is replaced by the same quantity of the polymer prepared in accordance with Example 6. A comparably effective anti-solar cream results.

EXAMPLE 50

An anti-solar milk in accordance with the present invention is prepared by admixing the following components:

| | |
|---|---|
| Polymer of Example 11 | 5g |
| Polymer of Example 6 | 5g |
| Sipol wax | 5g |
| Vaseline oil | 6g |
| Isopropyl myristate | 3g |
| Propyl p-hydroxybenzoate | 0.3g |
| Glycerin | 20g |
| Perfume | 0.5g |
| Water, q.s.p. | 100g |

EXAMPLE 51

An anti-solar aerosol foam composition in accordance with the present invention is prepared by admixing the following components:

| | |
|---|---|
| Polymer of Example 16 | 10g |
| Sipol wax | 3.5g |
| Vaseline oil | 6g |
| Isopropyl myristate | 3g |
| Methyl p-hydroxybenzoate | 0.3g |
| Glycerin | 10g |
| Perfume | 0.3g |
| Water, q.s.p. | 100g |

87g of the above composition are packaged in a conventional aerosol container under pressure together with 13g of dichlorodifluoromethane.

EXAMPLE 52

An anti-solar cream is prepared by admixing the following components:

| | |
|---|---|
| Polymer of Example 24 | 15g |
| Cetylstearyl alcohol | 2g |
| Glycerol monostearate | 4g |
| Cetyl alcohol | 4g |
| Vaseline oil | 5g |
| Butyl stearate | 5g |
| Propyleneglycol | 7g |
| Silicone oil | 0.125g |
| Nonionic polymer of high molecular weight sold under the mark POLYOX (in a 5% solution in water) | 3.5g |
| Methyl p-hydroxybenzoate | 0.3g |
| Perfume | 0.5g |
| Water, q.s.p. | 100g |

EXAMPLE 53

An anti-solar oil is prepared by admixing the following components:

| | |
|---|---|
| Polymer of Example 25 | 10g |
| Perfume | 0.4g |
| Butylated hydroxytoluene | 0.0625g |
| Colza oil, q.s.p. | 100g |

USE OF ANTI-SOLAR COPOLYMERS TO PROTECT DYES

Example 54

A hair setting lotion for coloring hair is prepared in accordance with the present invention by admixing the following components:

| | |
|---|---|
| Copolymer of Example 11 | 0.3g |
| Copolymer of vinylpyrrolidone/ vinylacetate, 70/30, M.W. = 40,000 | 2g |
| Ethyl alcohol | 50g |
| Dye - CI Basic Violet 1 (CI 42535) | 0.002g |

|  |  |
|---|---|
| Water, q.s.p. | 100g |

Example 55

A hair setting lotion for coloring hair is prepared in accordance with the present invention by admixing the following components:

| | |
|---|---|
| Copolymer of Example 16 | 0.3g |
| Copolymer of crotonic acid/vinyl acetate, 90/10, M.W. = 40,000 | 2g |
| Ethyl alcohol | 50g |
| Triethanolamine, q.s.p. | pH7 |
| Dye - CI Basic Violet 3 (CI 42555) | 0.002g |
| Dye - CI Basic Violet 1 (CI 42535) | 0.001g |
| Water, q.s.p. | 100g |

What is claimed is:

1. An anti-solar cosmetic composition comprising an aqueous, hydroalcoholic or oily solution containing an amount to assure protection against wave lengths of light in the erythematous zone of at least one anti-solar polymer containing in the macromolecular chain thereof at least one unit having the formula

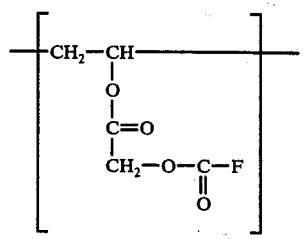

wherein F is a residue derived from an aromatic compound which imparts to the said polymer the ability to absorb wave lengths of light in the range of about 280–315 millimicrons and at least one unit derived from an ethylenically unsaturated monomer present in an amount of about 20–90 percent of the total weight of the polymer.

2. An anti-solar cosmetic composition comprising an aqueous, hydroalcoholic or oily solution containing an amount to assure protection against wave lengths of light in the erythematous zone of at least one anti-solar polymer containing in the macromolecular chain thereof at least one unit having the formula

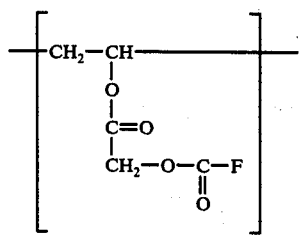

wherein
F is selected from

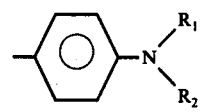  (1)

wherein $R_1$ and $R_2$ represent alkyl having 1-4 carbon atoms;

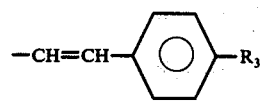  (2)

wherein $R_3$ is selected from the group consisting of hydrogen and methoxy;

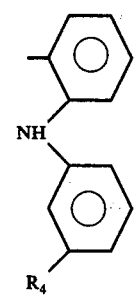  (3)

wherein $R_4$ is selected from the group consisting of $-S-CF_3$ and $-CF_3$;

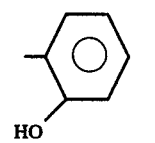  (4)

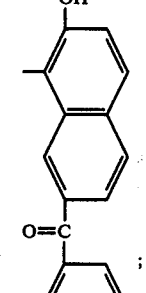  (5)

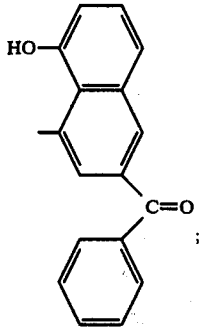  (6)

-continued wherein $R_4$ has the meaning given above;

-continued

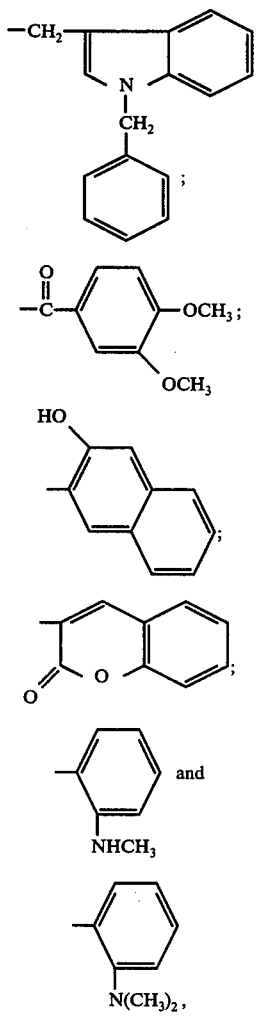

and at least one unit derived from an ethylenically unsaturated monomer present in an amount of about 20–90 percent of the total weight of the polymer.

3. The composition of claim 2 wherein said anti-solar polymer is present in amounts of about 0.2–20 percent of the total weight of the composition.

4. The composition of claim 2 in the form of a lotion, cream, milk, gel or aerosol packaged under pressure.

5. The composition of claim 2 which also includes at least one cosmetic adjuvant selected from the group consisting of fatty bodies, emulsifying agents, surfactant, perfume, silicone oil, pigment, dye and preservative.

6. An anti-solar cosmetic composition comprising an aqueous, hydroalcoholic or oily solution containing an amount to assure protection against wave lengths of light in the erythematous zone of at least one anti-solar polymer containing in the macromolecular chain thereof at least one unit having the formula

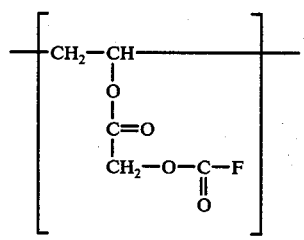

wherein F is

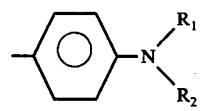

wherein $R_1$ and $R_2$ represent alkyl having 1–4 carbon atoms and at least one unit derived from an ethylenically unsaturated monomer present in an amount of about 20–90 percent of the total weight of the polymer.

7. The anti-solar cosmetic composition of claim 6 wherein the said polymer is a copolymer of vinyl stearate/vinyloxycarbonylmethyl 4-methoxy cinnamate/vinyloxycarbonylmethyl cinnamate/vinyloxycarbonylmethyl 4-N,N-dimethylamino benzoate.

8. The anti-solar cosmetic composition of claim 6 wherein said ethylenically unsaturated monomer is selected from the group consisting of
(a) N-vinylpyrrolidone,
(b) methacryloyl D-glucosamine,
(c) dimethylaminoethyl methacrylate,
(d) stearyl methacrylate,
(e) stearyl acrylate and
(f) vinyl stearate.

9. An anti-solar cosmetic composition comprising an aqueous, hydroalcoholic or oily solution containing an amount to assure protection against wave lengths of light in the erythematous zone of at least one anti-solar polymer containing in the macromolecular chain thereof at least one unit having the formula

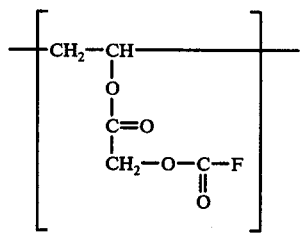

wherein
F is selected from

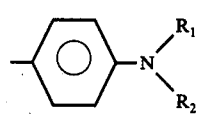 (1)

wherein $R_1$ and $R_2$ represent alkyl having 1–4 carbon atoms,

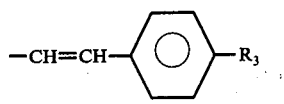 (2)

wherein R₃ is selected from the group consisting of hydrogen and methoxy;

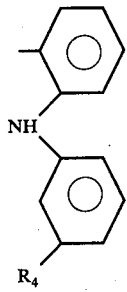 (3)

wherein R₄ is selected from the group consisting of —S—CF₃ and —CF₃;

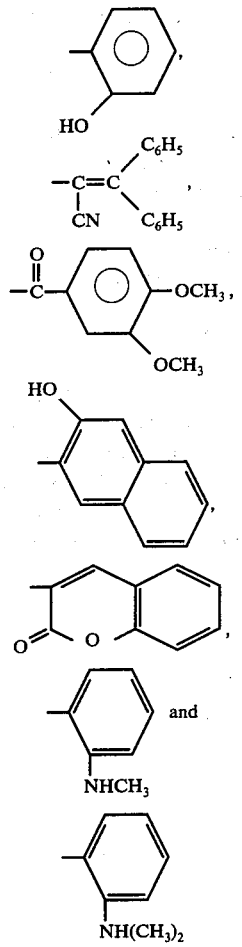

and at least one unit derived from an ethylenically unsaturated monomer present in an amount of about 20-90 percent of the total weight of the polymer.

10. An anti-solar cosmetic composition comprising an aqueous, hydroalcoholic or oily solution containing an amount to assure protection against wave lengths of light in the erythematous zone of at least one anti-solar polymer having the formula

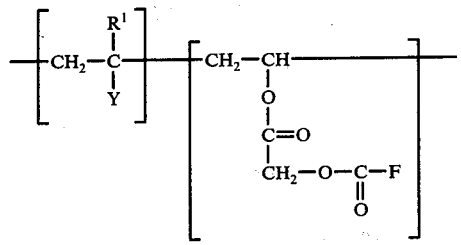

wherein
F is selected from the group consisting of

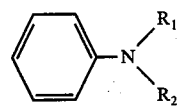 (1)

wherein $R_1$ and $R_2$ represent alkyl having 1-4 carbon atoms,

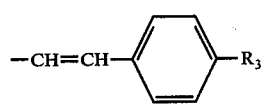 (2)

wherein $R_3$ represents hydrogen or methoxy,

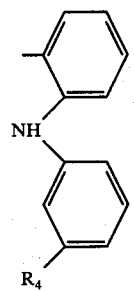 (3)

wherein $R_4$ represents —S—CF₃ or —CF₃, (4)

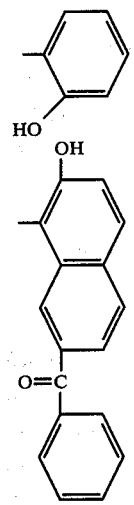

(5)

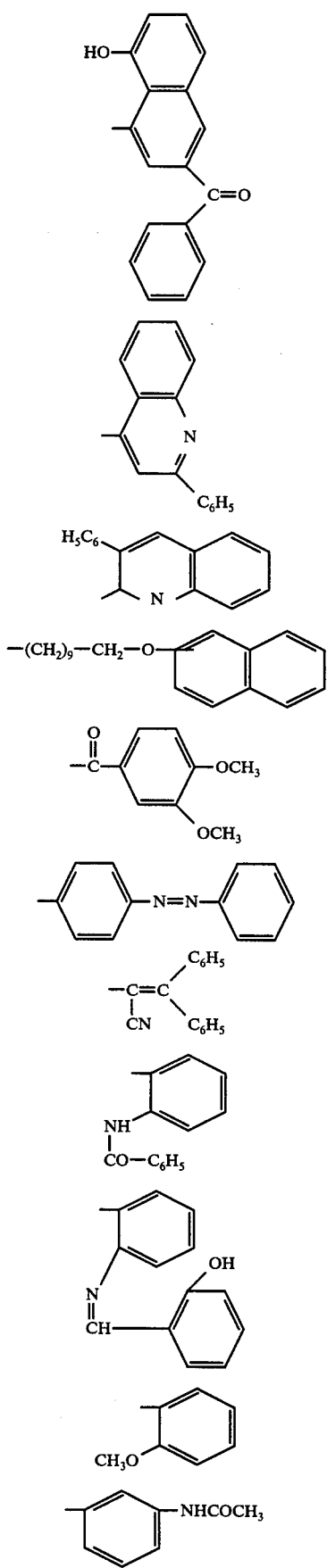
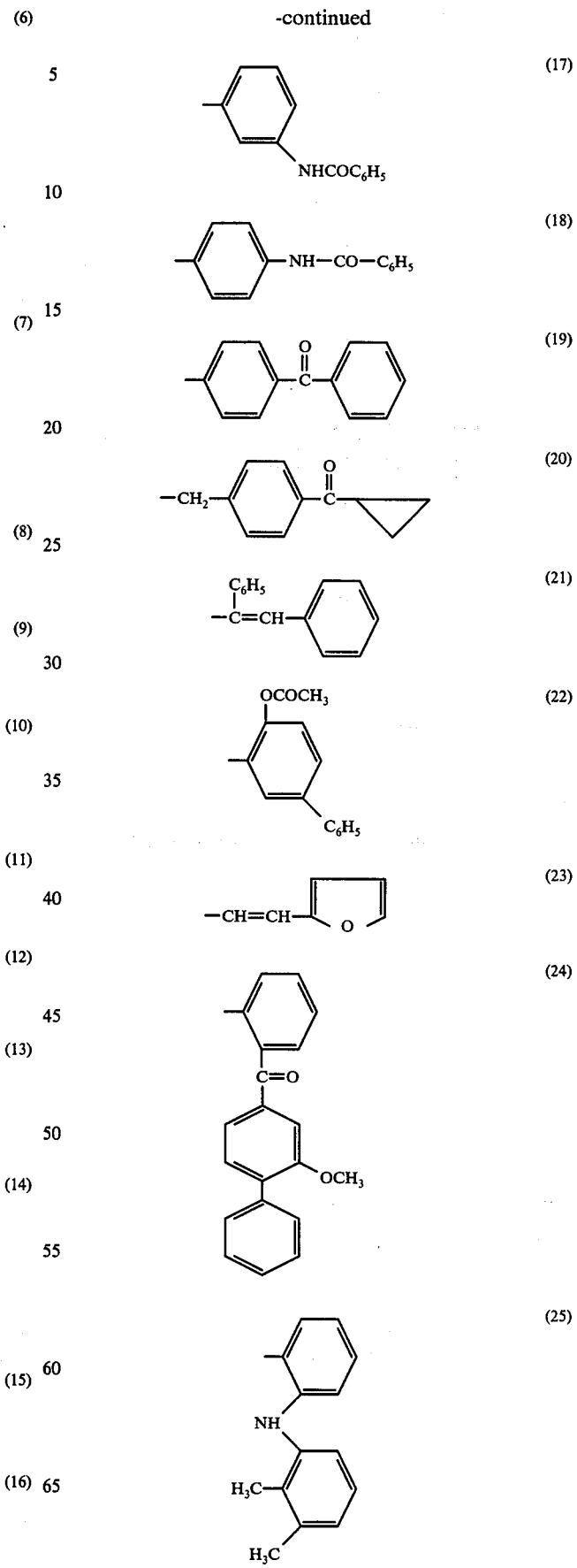

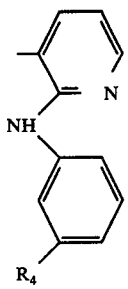 (26)

wherein $R_4$ has the meaning given above,

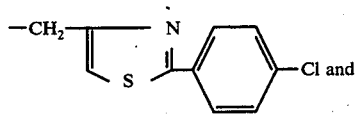 (27)

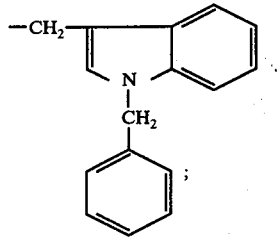 (28)

$R_1$ represents hydrogen or methyl and

Y represents a radical selected from the group consisting of

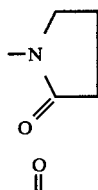 (i)

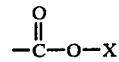 (ii)

wherein X represents D-glucosamine, dimethylamino ethyl, quaternized or not and $C_{18}H_{37}$, and

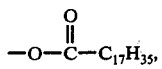 (iii)

wherein the unit

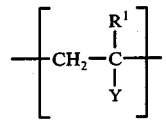

comprises between about 20 and 85% of the total weight of said polymer.

11. An anti-solar cosmetic composition comprising an aqueous, hydroalcoholic or oily solution containing an amount to assure protection against wave lengths of light in the erythematous zone of at least one anti-solar polymer containing in the macromolecular chain thereof at least one unit having the formula

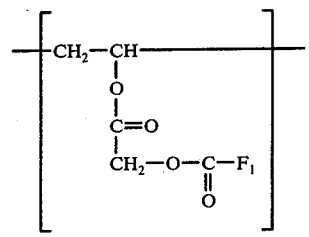

wherein $F_1$ represents a member selected from the group consisting of

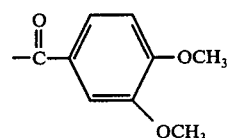 (1)

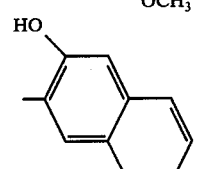 (2)

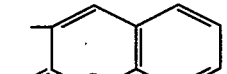 (3)

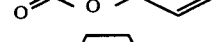 (4)

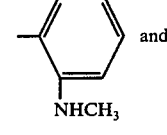 (5)

and at least one unit derived from an ethylenically unsaturated monomer, said unit being present in an amount between 20 and 80% of the total weight of said polymer.

* * * * *